(12) United States Patent
Thoes et al.

(10) Patent No.: US 7,273,484 B2
(45) Date of Patent: Sep. 25, 2007

(54) BLOOD WITHDRAWAL SYSTEM

(75) Inventors: Bruno Robert Thoes, Quierschied (DE); Michael Schabbach, Weinheim (DE); Hans Kintzig, Tiefenthal (DE); Peter Ruschke, Budenheim (DE); Hans Kuhr, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 317 days.

(21) Appl. No.: 10/913,638

(22) Filed: Aug. 6, 2004

(65) Prior Publication Data

US 2005/0090850 A1  Apr. 28, 2005

(30) Foreign Application Priority Data

Aug. 7, 2003 (DE) .................. 103 36 933

(51) Int. Cl.
*A61B 17/32* (2006.01)
(52) U.S. Cl. .................. 606/181; 600/573
(58) Field of Classification Search .................. None
See application file for complete search history.

(56) References Cited

U.S. PATENT DOCUMENTS

| 4,416,279 | A | | 11/1983 | Lindner et al. | |
|---|---|---|---|---|---|
| 4,442,836 | A | | 4/1984 | Meinecke et al. | 128/314 |
| 4,469,110 | A | | 9/1984 | Slama | 128/770 |
| 5,318,583 | A | * | 6/1994 | Rabenau et al. | 606/182 |
| 5,318,584 | A | * | 6/1994 | Lange et al. | 606/182 |
| 5,324,303 | A | | 6/1994 | Strong et al. | |
| 6,409,740 | B1 | | 6/2002 | Kuhr et al. | 606/182 |
| 6,419,661 | B1 | | 7/2002 | Kuhr et al. | 604/207 |
| 2002/0040230 | A1 | | 4/2002 | Kuhr et al. | |
| 2004/0092996 | A1 | * | 5/2004 | List et al. | 606/181 |
| 2005/0131441 | A1 | * | 6/2005 | Iio et al. | 606/182 |

FOREIGN PATENT DOCUMENTS

| DE | 42 12 315 A | 10/1993 |
|---|---|---|
| EP | 0569124 A1 | 11/1993 |
| EP | 0550585 B1 | 8/1994 |
| EP | 0 958 783 | 11/1999 |
| EP | 1034740 A1 | 9/2000 |
| EP | 1074219 A2 | 2/2001 |
| EP | 1 166 719 | 1/2002 |
| EP | 1254632 A1 | 11/2002 |
| EP | 1384438 A1 | 1/2004 |
| EP | 1 405 595 A1 | 4/2004 |
| JP | 2003-149780 | 5/2003 |

* cited by examiner

*Primary Examiner*—Glenn K. Dawson
(74) *Attorney, Agent, or Firm*—Richard T. Knauer; Roche Diagnostics Operations, Inc.

(57) ABSTRACT

The present invention generally relates to a blood withdrawal system for withdrawing blood for diagnostic purposes. The blood withdrawal system includes housing with a lancet, which can be moved within the housing. The housing also includes a lancet drive with a drive spring and a cocking mechanism that includes an actuation element. The blood withdrawal system of the present invention also includes a lancet ejection mechanism that can be moved from an active position to remove the lancet to a passive position where such removal of the lancet is not possible.

23 Claims, 5 Drawing Sheets

BLOOD WITHDRAWAL SYSTEM

REFERENCE TO RELATED APPLICATIONS

The present application claims priority to German Patent Application No. 10336933.3, filed Aug. 7, 2003, which is hereby incorporated by reference in its entirety.

TECHNICAL FIELD

The invention generally refers to a blood withdrawal system for withdrawing blood for diagnostic purposes.

BACKGROUND

Lancets are used in analytical-diagnostic applications to withdraw a small amount of blood from a part of the body (usually the finger or the earlobe) by pricking the lancet into the body part to generate a wound. If done manually, specially trained personnel are required for this purpose. However, puncturing is associated with considerable pain.

Blood withdrawal systems consisting of a puncturing device and corresponding lancets which are specifically adapted to the corresponding puncturing device have been in use for a long time. Typically, a housing of the puncturing device contains a lancet drive by which a lancet is punctured mechanically through the skin. The driving element for the puncturing motion is a spring. Early in the development very simple designs were common, in which the lancet was attached directly to one end of a compression spring which was arranged in an elongated housing. An example of such a lancing devise is shown in U.S. Pat. No. 4,469,110.

However, blood withdrawal systems of this type fail to satisfy the difficult requirements that must be met when the regular monitoring of certain analytic blood values are required. This particularly applies to diabetics who have to monitor their blood sugar level frequently in order to keep this level within certain limiting values by suitably adapting the insulin injections. Scientific investigations have shown that an intensive therapy involving at least four blood analyses per day can dramatically reduce the extremely severe late consequences of diabetes mellitus such as retinopathy which eventually leads to blinding of the patient.

However, with such intensive therapy it is desirable that the withdrawal of blood is associated with as little pain as possible. Numerous blood withdrawal systems aiming for an improvement in this area have been developed.

A typical withdrawal of blood by means of a blood withdrawal system requires two basic functions. Firstly, the puncturing device must be brought to a state in which it is ready for puncturing by tensioning the drive spring. This is called the "cocking phase". Subsequently, the lancet drive is triggered and the relaxing motion of the drive spring drives the lancet. This is called the "drive phase".

In previous blood withdrawal systems, the puncturing phase was the kinematic reverse of the cocking phase. In other words, the drive was cocked simply by pushing the lancet, after puncturing, back into its original position in which the spring was tensioned.

However, better results, in particular with regard to the lowest possible pain level while keeping the handling simple, are achieved when the lancet drive is designed such that the two functions are uncoupled from each other. Accordingly, it is preferable that in a cocking phase, the motion of an actuation element of a cocking mechanism is transmitted by an input-side coupling mechanism to the drive spring such that the spring is tensioned. And in a drive phase, the relaxing motion of the drive spring is transmitted by an output-side coupling mechanism to the lancet such that the lancet performs the puncturing motion at high speed.

The two coupling mechanisms usually consist of different structural elements. In any case, the motions performed during the two phases differ from each other (rather than being the kinematic reverse of the other phase). Blood withdrawal systems of this type are known, for example, from the following publications: U.S. Pat. No. 4,442,836; U.S. Pat. No. 5,318,584; U.S. Pat. No. 6,409,740; U.S. Pat. No. 6,419,661; and EP 1 254 632 A1.

Despite the extensive development efforts which resulted in the constructions described in these documents and numerous others, there is a strong interest to have a blood withdrawal system which optimally satisfies the difficult and to some extent contrary requirements i.e minimal pain sensation, simple handling, compact design as slim as possible, cost-efficient fabrication. Therefore, there is a need in the industry to improve the design of such blood withdrawal systems that will satisfy such requirements.

SUMMARY

The present invention relates to a blood withdrawal system which comprises a housing with an exit opening for the tip of a lancet, which is mobile within the housing along a pre-determined puncturing path. The system also comprises a lancet drive with a drive spring and a cocking mechanism.

The cocking mechanism including an actuation element which is coupled to the drive spring via an input-side coupling mechanism such that the drive spring is tensioned in a cocking phase of the motion of the lancet drive upon motion of the actuation element. The drive spring is coupled to the lancet via an output-side coupling mechanism such that the lancet, during a drive phase of the motion of the lancet drive, is moved at high speed along the pre-determined puncturing path in the puncturing direction driven by the relaxing motion of the drive spring until the tip of the lancet exits out of the exit opening to generate a wound.

The actuation element of the cocking mechanism is coupled to a track control mechanism comprising a control track part and a control traveler. The control traveler performs a relative motion with respect to the control track part during at least a part of the cocking phase, in which motion it travels along the control track of the control track part whereby at least a part of the motion of the lancet drive is controlled.

According to the invention an additional control track mechanism is provided in addition to the coupling mechanisms effecting the transmission of force from the actuation element to the drive spring (cocking phase) and from the drive spring to the lancet (drive phase). This additional control track mechanism is coupled to the actuation element of the cocking mechanism and controls at least a part of the motion of the lancet drive. It consists of two parts, which are designated components of the track control mechanism, namely a control track part and a control traveler. Its controlling or steering effect is based on an interaction of the control track part and the control traveler with the lancet drive during the motion of the lancet drive. This interaction includes a motion of the control traveler relative to the control track, in which the control traveler follows, i.e. travels along, the control track and thereby affects a lancet drive controlling or steering function during at least a part of the cocking phase and/or in the puncturing phase.

The required guidance of the control traveler along the control track can be achieved by different constructive measures. The control track can be formed by a groove in the control track part whose width is adapted to the dimensions of the control traveler such that the latter is guided precisely within the control track. The guiding effect can also be achieved by implementing the control track in the form of a slide surface against which the control traveler is pressed by spring action. In any case, one of the components is coupled to the actuation element of the cocking mechanism such that it is moved synchronously with the actuation element. The coupling can be rigid or movable. In the case of a movable coupling, common coupling elements, such as levers, can, for example, be used to connect the actuation element of the cocking mechanism to the "input-side" component of the track control mechanism to which the actuation element is coupled. Preferably, this input-side component is the control track part, whereas the output-side component of the track control mechanism (which is coupled to the lancet drive such that it transmits the steering effect of the track control mechanism to the lancet drive) is preferably formed by the control traveler.

The relative motion of the control traveler with respect to the control track part can be realized by different combinations of motions of the two components of the track control mechanism. For example, in a section of the relative movement the control track part can be moved, while the control traveler is stationary with respect to the housing of the puncturing device. In other sections, the movement along the control track can be based on a motion of the control traveler while the control track part is stationary. Finally, both components of the track control mechanism can be moved simultaneously. Details depend on the individual case at hand. Preferably, the control track part is moved during at least a part of the desired control period in a translational motion, whereas the control traveler preferably moves at least partly on a circle.

The actuation element of the cocking mechanism is usually realized in the form of a cocking button which projects from the rear end (opposite from the puncturing opening) of an elongated housing and generally is actuated by pressing with the thumb. However, the invention is also suitable for use with other actuation elements of the cocking mechanism, e.g. a pusher which is movable along the wall of the housing or an actuation element which can be moved by pulling and is formed, for example, by the rear part of the housing. Hereinafter, reference shall be made to a cocking button for exemplary purposes without limiting the generality.

The track control mechanism which is separate from the mechanical elements required in the lancet drive for cocking (by transmission of force from the actuation element to the lancet drive), but coupled to the cocking button of the lancet drive achieves several advantageous functions.

Due to the fact that the track control mechanism is coupled to the cocking button of the lancet drive, but is independent of the transmission of force, it becomes possible to assign additional functions (aside from the cocking of the lancet drive) to the cocking button, such as, for example, the triggering of the drive phase (puncturing motion) or the removal of a used lancet from the puncturing device. This allows "one-hand operation".

The track control mechanism can be used to establish defined intermediate positions of the cocking button, which characterize intermediate stages in the handling of the blood lancet system, and thus clearly indicate to the user the status of the system (for example, "relaxed", "cocked").

By providing a "reversing section" in the control track it is possible to realize an operation of the cocking button of the "push-button switch type", as will be illustrated in more detail below.

By means of one-way sections of the control track, which are also described in more detail below, it is possible to ensure that the journey of the traveller along the control track is possible in only one direction and consequently to achieve a certain sequence of steps without undesired repetition. An important example is a "re-cocking lock" preventing repeated cocking of the drive.

The blood withdrawal system of the present invention also includes a lancet ejection mechanism with a release element which is borne in the housing such that it can be switched between a passive position and an active position. The lancet ejection mechanism is activated when the release element is in its active position such that actuating an actuation button of the lancet ejection mechanism removes a used lancet from the housing. The lancet ejection mechanism is inactivated when the release element is in its passive position such that actuating the actuation button does not lead to the ejection of a lancet.

The front end of the housing with the puncturing opening is formed by a cap, which can be removed in order to remove used lancets. The cap, when attached, interacts with the release element such that it is in its passive position, and the release element is switched to its active position upon removal of the cap.

The term "ejection mechanism"0 is generally used to designate a combination of mechanical elements which together allow removal of the lancet from the puncturing device by moving an actuation button without having to touch the lancet. In this context, "ejection" does not mean that the lancet is accelerated during its removal from the device. Rather, it is usually considered to be advantageous if the ejection mechanism only opens a lancet holder of the puncturing device such that the lancet falls out by the effect of gravity.

The ejection mechanism is non-functional as long as the cap is attached to the front end of the housing of the puncturing unit. The mechanism is activated only upon removal of the cap whereby possible mishandling is prevented. Furthermore it is possible to use the cocking button simultaneously as actuation button of the ejection mechanism without adversely affecting its other functions, for example by restricting its possible path of motion. This is also explained in more detail below.

It is preferable to use both features of the invention in lancet systems whose lancet drive includes a drive rotor which is driven by the drive spring and rotates about an axis, wherein the drive rotor, driven by the drive spring in the drive phase of the lancet drive, performs a rotational motion which is transformed into the puncturing motion by the output-side coupling mechanism. A rotor drive of this type is used, for example, in U.S. Pat. No. 5,318,584; U.S. Pat. No. 6,409,740 and U.S. Pat. No. 6,419,661.

It is particularly preferable to use the present invention in combination with a special rotor drive as described in EP 1384438 A1 (and its equivalents: U.S. Ser. No. 10/445,606 and JP 149780/2003). The entire content of the previous application is incorporated herein by reference.

In the rotor drive described therein, the end of the drive spring which is remote from the drive rotor is supported by a rotatable tensioning element, which can be rotated in the same direction, in which the drive rotor rotates during the drive phase, in order to tension the drive spring while the rotation of the drive rotor is inhibited. The tensioning element is locked against a reverse motion during the drive phase such that the drive rotor performs a rotational motion after the inhibition is released, which rotational motion is transformed into the puncturing motion by the drive-side coupling mechanism. In such a drive the mentioned elements are rotated in the same direction in an alternating manner during the cocking phase and during the drive phase. This principle is designated "One Way Alternating Drive and Cocking", or OWADAC for short.

The invention is illustrated in more detail hereafter on the basis of exemplary embodiments shown in the figures. The illustrated and described features can be used individually or in combination to create further preferred embodiments of the invention. In the figures:

DETAILED DESCRIPTION

The following description of the preferred embodiment is merely exemplary in nature and is in no way intended to limit the invention or its application or uses.

Figure 7:
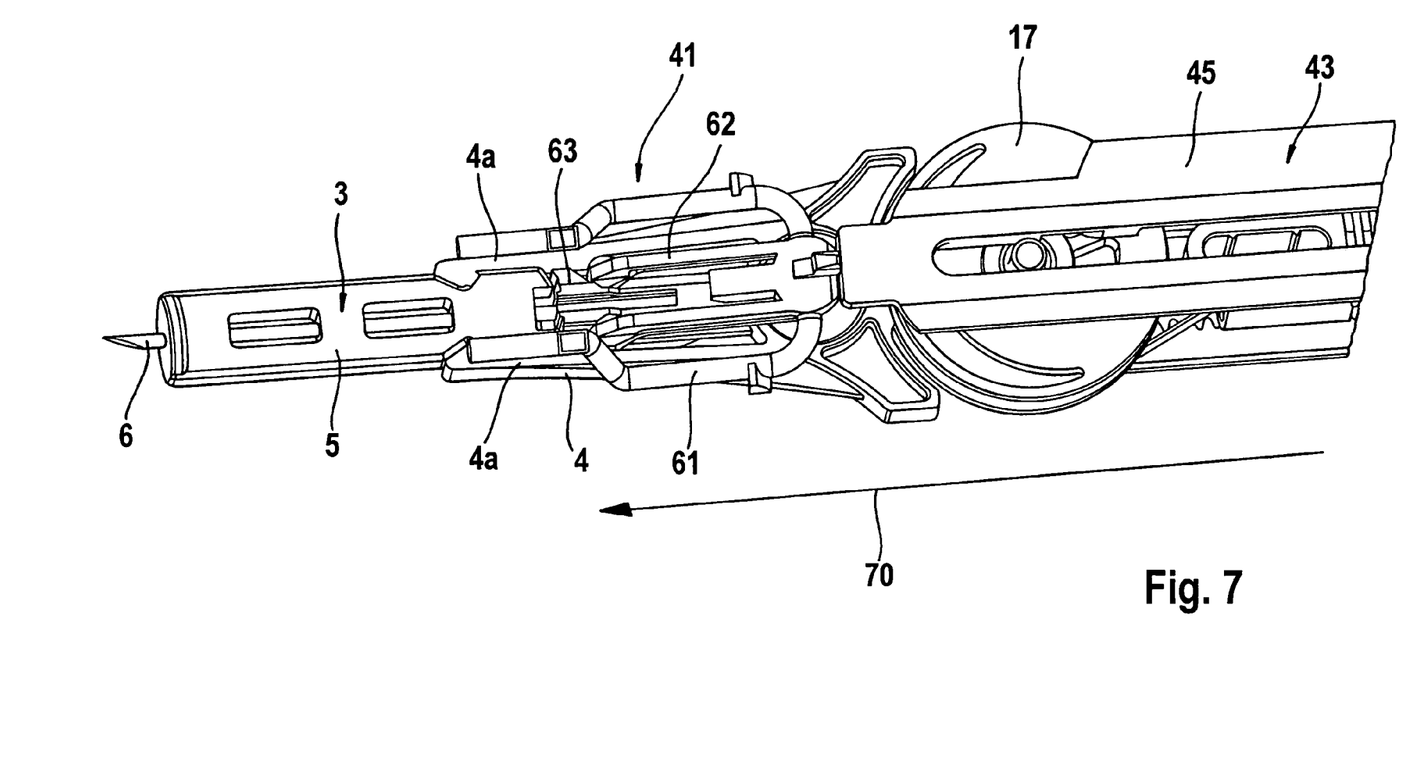
FIG. 7 shows a perspective view of a part of the blood withdrawal system shown in FIG. 1 as seen from the other side ("control side")

The blood withdrawal system 1 shown in the figures consists of a puncturing device 2 and lancets 3 (shown in FIG. 7). The mounting and the guide means for a lancet 3 in puncturing device 2 are shown in FIG. 7. Holding latches 4a of a lancet holder 4 encompass the rear part of lancet body 5. A lancet tip 6 projects forward from the lancet body 5.

During the puncturing process, the lancet holder 4 is guided by means of a housing part (not shown) serving as guide means. Thereby indirectly the required guidance of the lancet on a pre-determined puncturing path (here along the main axis A of puncturing device 2) is provided. Thus, the lancet is indirectly guided via the lancet holder 4.

However, the invention can also be used with puncturing devices, in which the lancet is "directly guided", i.e. resides directly in a part of the housing providing the required guidance during the puncturing motion (a cartridge containing a plurality of lancets, for example). More details can be taken from EP 1384438 A1.

The housing 8 of puncturing device 2 contains a lancet drive 9. The lancet drive 9 moves the lancet in a high speed along the puncturing direction (shown by arrow 10) until the lancet's tip exits from an exit opening 11, while a contact surface 12 of puncturing device 2, which surrounds exit opening 11, is pressed against a body part (not shown herein). This generates a wound in the body part for the withdrawal of blood. The housing 8 of the puncturing device preferably has an elongated shape. The end with exit opening 11 is designated herein as front end, and the opposite end is designated rear end. The front end of housing 8 is formed by a removable cap 7.

Figure 1:
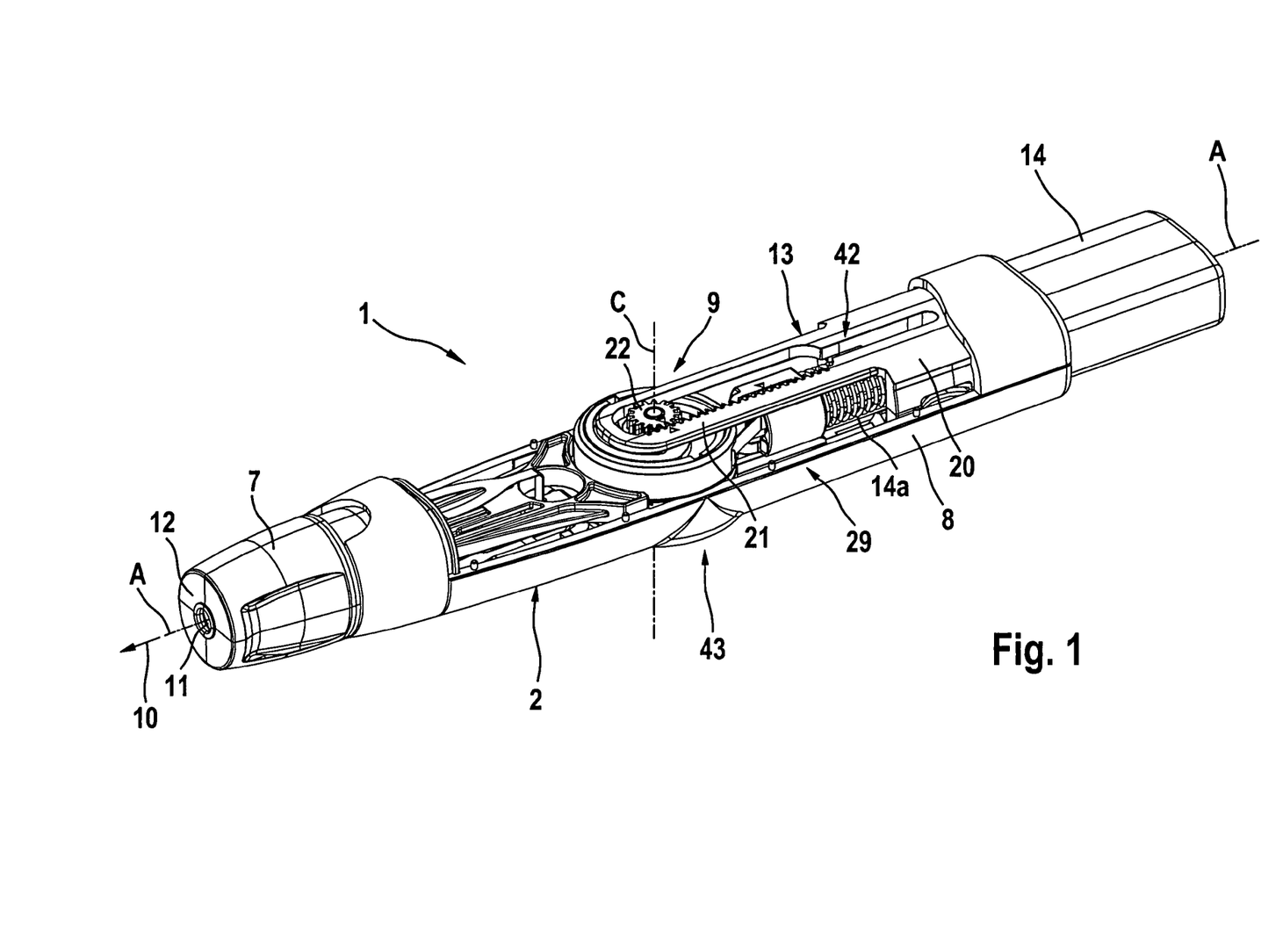
FIG. 1 shows a partially cut-open perspective view of a blood withdrawal system according to the invention.
Figure 2:
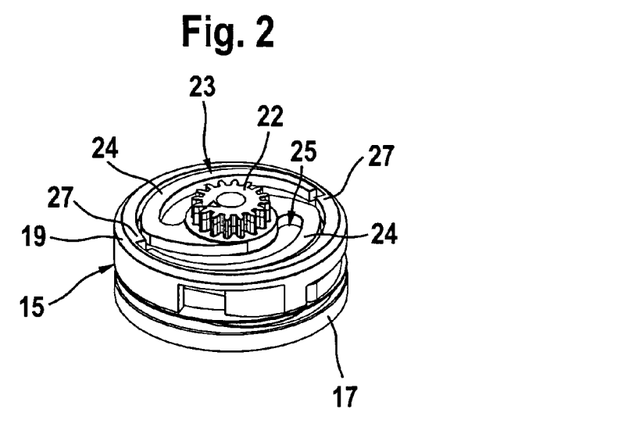
FIG. 2 shows a perspective view of a drive module of the lancet drive used in the blood withdrawal system according to FIG. 1.
Figure 3:
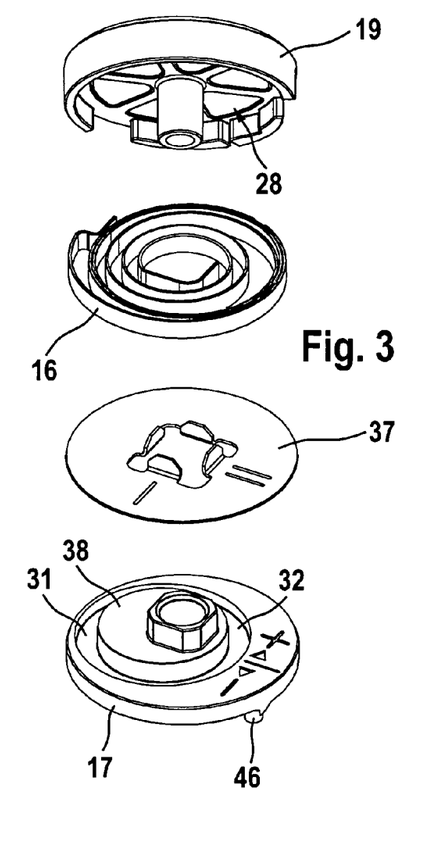
FIG. 3 shows an exploded perspective view of components of the module of FIG. 2.
Figures 4, 6:
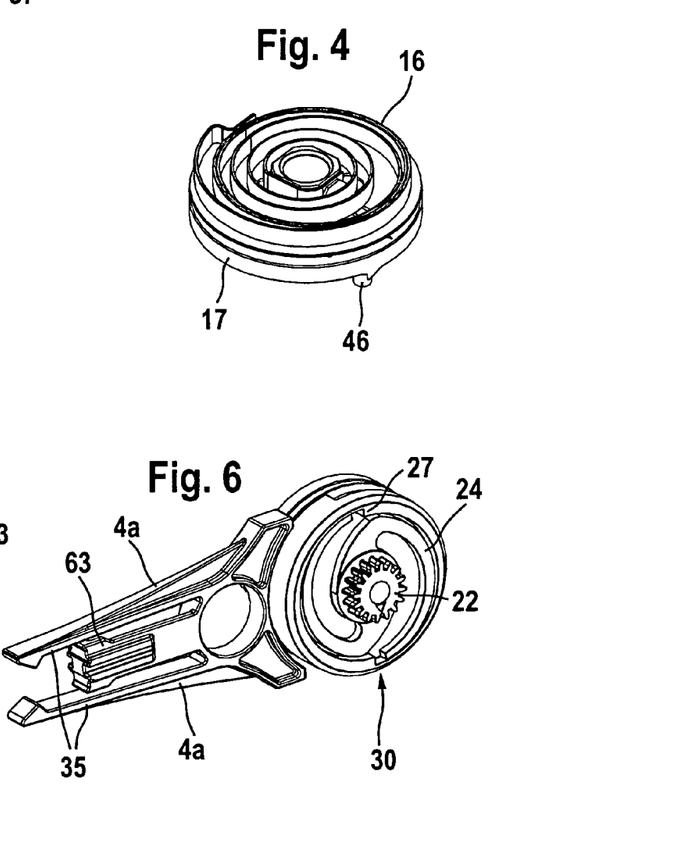
FIG. 4 shows a perspective view of a module according to FIG. 2 in a partially assembled state.
FIG. 6 shows a perspective view of a subunit of the blood withdrawal system according to FIG. 1 consisting of a drive module according to FIG. 2 and a lancet holder according to FIG. 5.
Figure 5:
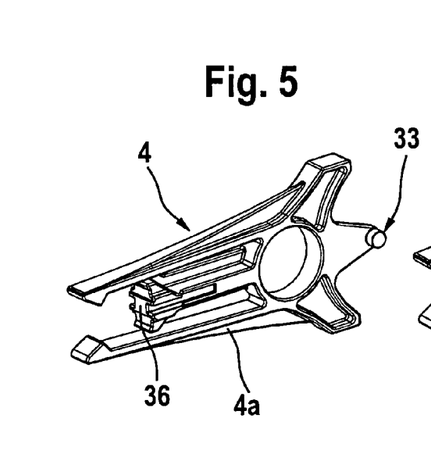
FIG. 5 shows a perspective view of a lancet holder of the blood withdrawal system according to FIG. 1.

FIGS. 1 to 6 illustrate the design features of the lancet drive 9, which are required for the transmission of force during the cocking phase and during the drive phase. As shown, during the cocking phase, in order to tension the spring, the force exerted onto a cocking button 14 is transmitted by a cocking mechanism (designated in its entirety as 13) to a drive spring 16 (shown in FIG. 4). Preferably as shown in FIG. 2, the drive spring 16 is integrated into a drive module 15. During the drive phase, the drive spring 16 relaxes and drives a drive rotor 17 whose rotational motion, in turn, transforms into the translational puncturing motion of lancet holder 4. This transmission of force in the present invention is identical to that described in EP 1384438 A1.

The components of drive module 15 include a drive rotor 17 and a tensioning element 19. As shown specifically in FIG. 1, the drive module 15 and the dive rotor 17 are rotatable about a common axis C which extends perpendicular to the puncturing direction 10 and to the longitudinal axis A of the puncturing device 2.

In order to cock the lancet drive 9, the cocking button 14, which is movable in a translational motion, is pushed together with a force transmission part 20 in puncturing direction 10. One component of the force transmission part 20 is a toothed rack 21 driving a pinion gear 22 which is coaxial to the tensioning element 19. The pinion gear 22 is connected to the tensioning element 19 by means of a free-wheel device 23 such that the two parts are coupled to each other during the cocking motion, but uncoupled from each other during the return of the force transmission part 20, and cocking button 14, under the effect of a restoring spring 14a.

As shown in FIG. 2, the free-wheel device 23 is realized by means of two elastic latches 24, which are connected to the pinion gear 22. The latches 24 are located in a recess 25 of the tensioning element 19, the recess 25 face away from the drive rotor 17 and have two limit stops 27, at which the ends of the latches 24 abut in the coupling rotation direction (clockwise in FIG. 2), whereas the pinion gear 22 can rotate freely relative to the tensioning element 19 in the reverse direction.

The rotation of the tensioning element 19 tensions the drive spring 16, which is a helical spring borne in a recess 28 of the tensioning element 19 which recess faces towards the drive rotor 17. The force transmission part 20 with toothed rack 21, the pinion gear 22, the free-wheel device 23 and the actuation element 10 jointly form an input-side coupling mechanism 29, which transmits the force exerted onto the cocking button 14 to the drive spring 16 during the cocking phase.

The output-side coupling mechanism 30, which transmits the force of the spring 16 to the lancet 3 during the drive phase, includes a control curve 31 which is formed by a circumferential groove 32. In the example shown, the control curve 31 takes the shape of a circle which is eccentric with respect to axis C. A control pin 33, which is a component of the lancet holder 4, travels along the control curve 31 during the rotation of drive rotor 17. To fix a lancet, the lancet holder 4 is provided with elastic arms 35 and a limit stop element 36, whose shapes are adapted to the corresponding shape of the lancet body 5 such that lancet 3 is held in an exactly reproducible longitudinal position within lancet holder 4.

The rear end of lancet holder 4 with control pin 33 extends through a circumferential slit of the drive module 15 in such a manner that there is no interference with the rotational motion of the components of module 15. In the embodiment shown this is achieved by means of a separating disc 37 made from metal, which is placed on a plateau 38 of drive rotor 17 in such a manner that a circumferential gap with a sufficient width to accommodate lancet holder 4 remains between the disc and the parts of the rotor 17 which are radially outwards from control curve 31. In the embodiment of the lancet drive 9 shown, the motion phases of the drive follow the OWADAC principle as follows:

During the cocking phase, the rotatable tensioning element 19, driven by cocking button 14 via force transmission part 20 by means of toothed rack 21 and pinion gear 22, rotates in a predetermined direction (clockwise in FIGS. 1 and 2), whereby the drive spring 16 is tensioned, while the rotation of drive rotor 17 is inhibited (by means of the trigger mechanism described in more detail below).

In the drive phase, the drive spring 16 drives the drive rotor 17 (after release of the inhibition), while simultaneously the tensioning element 19 is locked against a reverse rotation (for example by an elastic catch, not shown herein, engaging a recess of tensioning element 19).

Figure 8:
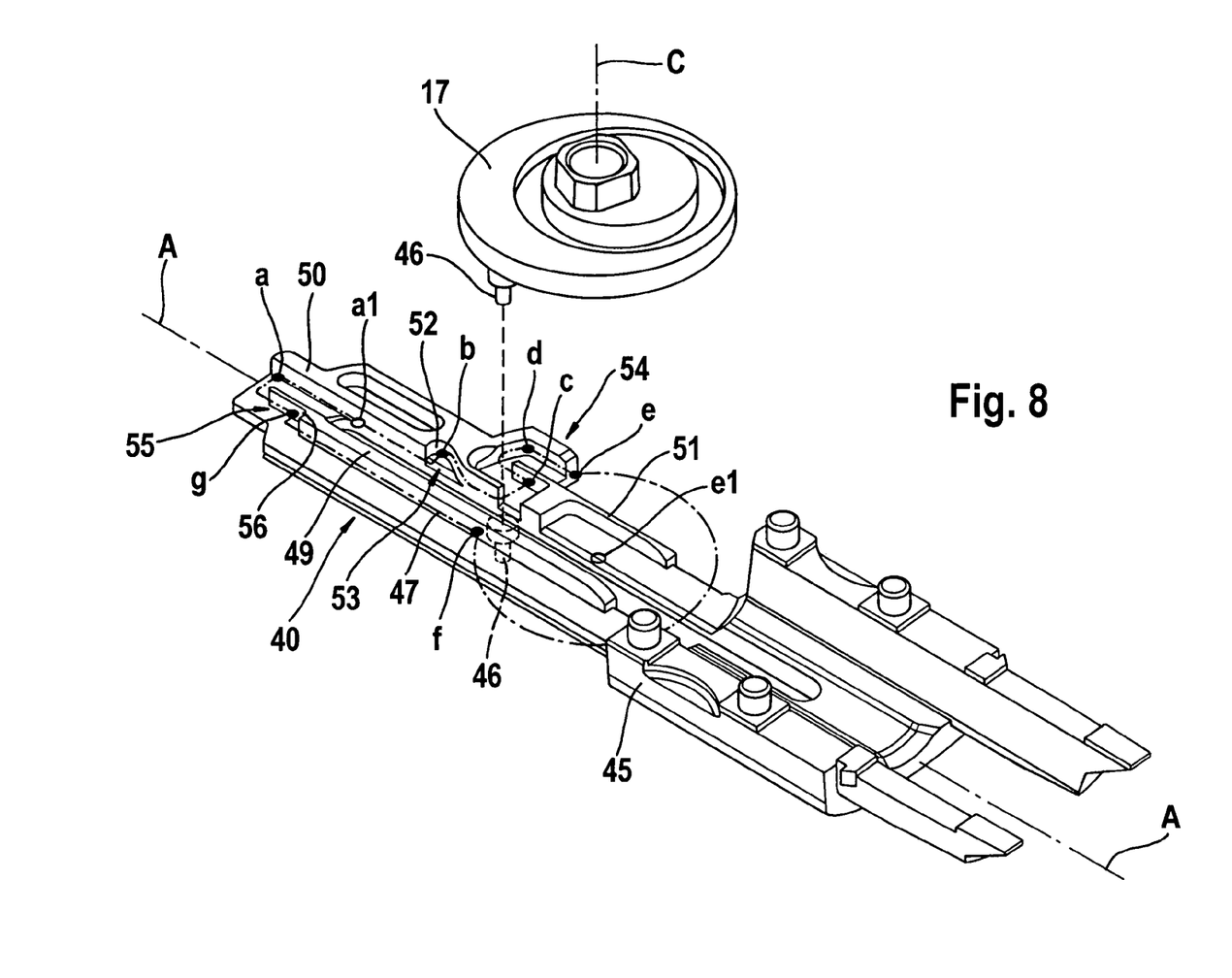
FIG. 8 shows an exploded view of a control track part and a drive rotor with control traveller.
Figure 9:
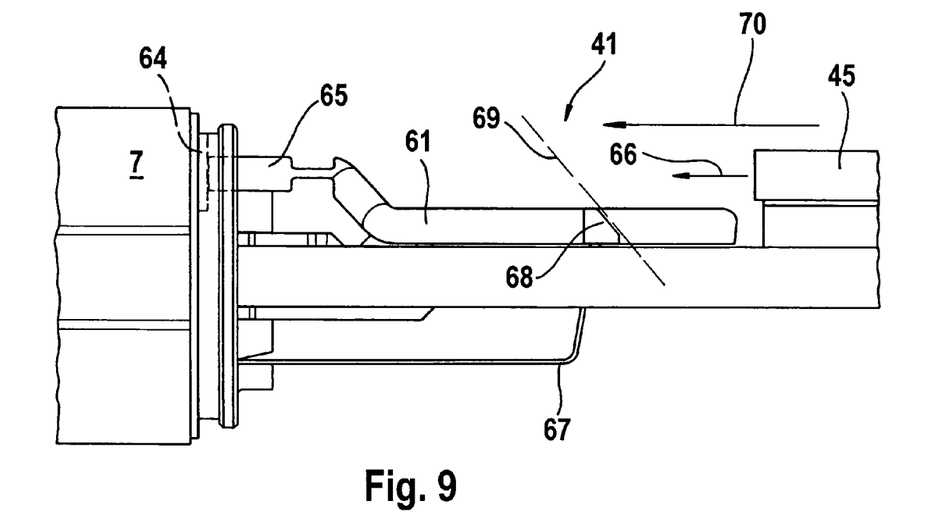
FIG. 9 shows a side view onto parts of an ejection mechanism with a release element in its passive position.

FIGS. 7 to 9 show the essential design elements of the track control mechanism 40 and the ejection mechanism 41, which are located, relative to drive rotor 17, on the side of puncturing device 2, which is opposite from the drive side 42 shown in FIG. 1 and is called control side 43.

The components of the track control mechanism 40 include a control track part 45 and a control traveler 46, which, in the embodiment shown, is a pin fixed to drive rotor 17. Because the control traveler 46 is fixed to the drive rotor 17, it can move only on a circular path about axis C thereof. Drive spring 16 exerts a torque (which varies in magnitude depending on its tensioning state, but always acts in the same direction) onto drive rotor 17 and thereby on control traveler 46 (in clockwise direction in the Figures).

In the assembled state, drive rotor 17 is located adjacent to the control track part 45 in such a manner that the control traveler 46 is positioned within a control track 47 of control track part 45 (this position of the control traveler 46 is indicated by broken lines in FIG. 8). A relative movement of control traveler 46 with respect to the control track part 45 results, on the one hand, when the control track part 45 is moved parallel to the longitudinal axis A of the puncturing device 2 and, on the other hand, by means of the motion of the control traveler 46 on a circular path about axis C. The translational motion of control track part 45 results from the coupling thereof with cocking button 14. In the preferred embodiment shown, the control track part 45 and the force transmission part 20 with toothed rack 21 are manufactured as one part and are formed approximately U-shaped such that in the assembled position the two legs of the U extend on the two sides of drive module 15, i.e. force transmission part 20 on drive side 42 and control track part 45 on guide side 43. The rear end of components 20, 45, which are connected to each other, is attached to cocking button 14 such that both parts are moved equally in a translational motion by actuation of cocking button 14.

Due to the actuation of cocking button 14 and the biasing action of the drive spring (resulting in a rotational motion of the drive rotor 17), the control traveler 46 travels along a control path 47, shown as dash-dot lines in FIG. 8, as defined by control profiles 49, 50, 51 embossed into control track part 45. The most important functional positions of the control track are identified in FIG. 8 by means of letters to which reference is made in the following explanation:

a) This is the initial position of the traveller 46 when the lancet drive is not loaded and the cocking button projects the farthest from housing 8. In this state the axis C of the drive rotor 17 is in position a1.

b) Here the control traveller 46 is positioned in a pocket 52 of the guide profile 50, which is shaped such that the control traveller 46 can be driven out only in one direction (continuing the previous motion). The section of control track 47 defined by pocket 52 is called one-way section 53, since the control traveller, once driven into the one-way section 53, can be driven out only in one direction. Thus, the control traveller 46 is capable of a relative motion with respect to the control track part 45 only in one direction of control track 47 beyond one-way section 53. This arrangement provides a safety function since multiple cocking of the lancet drive, which may lead to damage, is prevented.

c) When the cocking button 14 is depressed further (resulting in a forward motion of control track part 45), the control traveller 46 is driven by the action of the drive spring to this position in front of a locking wall formed by the guide profile 51, which prevents further depression of the cocking button.

d) When cocking button 14 is released, resulting in a rearward motion of control track part 45, the control traveller reaches this position, which corresponds to a stable intermediate position and in which the lancet drive is ready to be triggered, i.e. for starting the drive phase. Here, the cocking button is in a position which clearly differs from its initial position (corresponding to control track position a) and can additionally be labeled (e.g. by a color mark on the shaft of the cocking button 14). Thereby it is unambiguously indicated to the user that the device is in its cocked state and ready for use.

The section of the control track between the positions c and e forms a reversing section 54. Because of the U-shape of this section, the control traveller 46 can be driven out of reversing section 54 only after performing a relative motion with respect to control track part 45 in the reverse direction of the previous motion. This provides for actuation of the cocking button with a stable intermediate position as with a push-button switch.

e) By depressing the cocking button 14 again, the control traveller 46 reaches this position, in which the contact between control traveller 46 and control track part 45 is interrupted. The control traveller is free allowing the drive rotor 17 to perform a rapid rotational motion about rotor axis C, which at this point of time is in position e1. The cocking button 14 therefore performs two functions, namely cocking and triggering.

f) The rotational motion is terminated when the control traveller 46 again contacts control track part 45 (i.e., in the case shown, its guide profile 49) in this position.

g) Under the action of the restoring spring 14a, the cocking button 14 and, jointly with the button, the control track part 45 are moved backwards again, whereby the control traveller reaches its initial position via this position. Position g again marks a one-way section 55, in which the control traveller is positioned in a pocket 56, which prevents a motion against the predetermined direction of control track 47.

Figure 10:
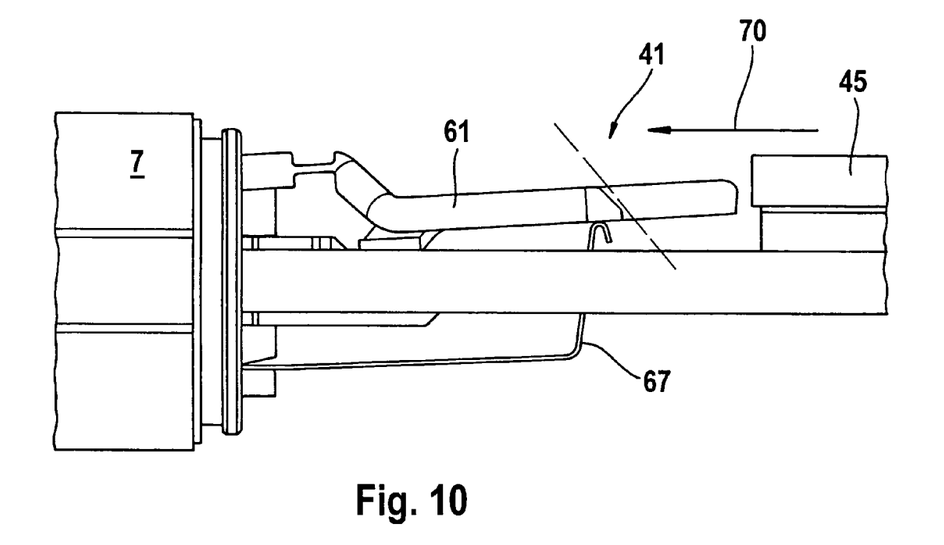
FIG. 10 shows a side view onto parts of an ejection mechanism with a release element in its active position.

FIGS. 8 to 10 show the essential parts of the ejection mechanism, which in its entirety is designated 41 and consists, in the embodiment shown, of cocking button 14, control track part 45 and a release element 61. These elements are each borne in such a manner that they can be displaced in a translational motion in the puncturing direction 10 (and therefore in the direction of axis A of the device). They form a force transmission chain, which is symbolically indicated by arrow 70 and by which the motion of an actuation button of the lancet ejection mechanism is transmitted to the lancet holder 4 in such a manner that the lancet 3 is released and can fall out of the holder 4 by the action of gravity. In the embodiment shown, the actuation button of the lancet ejection mechanism simultaneously is the actuation element of the cocking mechanism, i.e. the cocking button 14. Though this is not absolutely required, it is particularly preferred. In this embodiment a single actuation button performs three functions (cocking, triggering, ejecting).

The release of the lancet in the embodiment shown is achieved by pushing sliding latches 62, which are provided on the release element 61, between the elastic latches 4a of the lancet holder 4 and a counter-bearing 63 of the lancet holder 4 which extends oblique-outwards. This causes the holding latches 4a to be pressed apart and release the lancet 3.

As long as the removable cap 7, which forms the front end of housing 8, is attached, the lancet ejection mechanism 41 is inactivated, i.e. actuation of the cocking button 14 does not result in ejection of the lancet. Removal of the cap switches the lancet ejection mechanism 41 to its active state.

The switching between the active and the passive state is achieved by means of a change in the position of the release element as shown in FIGS. 9 and 10. In FIG. 9, the release element is in its passive position, in which the force transmission chain 70 between the cocking button and the lancet is interrupted: cap 7 includes a counter-bearing 64, shown by dashed lines in FIG. 9, which, as long as the cap is attached, pushes against the front end of an actuation part 65 on the release element 61. This causes a pressure part 68 of the release element to be pressed against an oblique surface 69 which is fixed relative to the device and shown only schematically in FIG. 9. The release element is held in the horizontal position shown in FIG. 9. If the front end of control track part 45 is displaced, as indicated by arrow 66, this motion is not transmitted to the release element 61, since the two parts are not mutually engaged.

In contrast, when the cap 7 is removed, the pressure exerted by the counter-bearing 64 on the actuation part 65 ceases and the release element 61 is moved under the action of a leaf spring 67 to the position shown in FIG. 10. In this position, the rear end of release element 61 is within the movement path of control track part 45, such that a forward motion of the control track part 45 (upon actuation of the cocking button 14) is transmitted to the release element 61 and thereby also to the lancet.

As any person skilled in the art will recognize from the previous description and from the figures and claims, modifications and changes can be made to the preferred embodiment of the invention without departing from the scope of the invention as defined in the following claims.

What is claimed is:

1. A Blood withdrawal system for withdrawing blood for diagnostic purposes, the system comprising:

a housing, wherein a lancet can be moved within the housing along a pre-determined puncturing path to perform a puncturing motion; and a lancet drive with a drive spring and a cocking mechanism;

wherein the cocking mechanism includes an actuation element, wherein the actuation element is coupled by an input-side coupling mechanism to the drive spring, said input-side coupling mechanism effecting a transmission of force from the actuation element to the drive spring, such that the drive spring is tensioned when the actuation element is moved during a cocking phase of the lancet drive;

wherein the drive spring is coupled by an output-side coupling mechanism to the lancet, said output-side coupling mechanism effecting a transmission of force from the drive spring to the lancet, such that the lancet during a drive phase of the lancet drive, is driven by the relaxing motion of the drive spring at a high speed along the pre-determined puncturing path to perform the puncturing motion to generate a wound; and wherein the actuation element is coupled to a track control mechanism, said track control mechanism being additional to the input-side coupling mechanism effecting the transmission of force from the actuation element to the drive spring and additional to the output-side coupling mechanism effecting the transmission of force from the drive spring to the lancet, the track control mechanism comprising a control track part and a control traveler, wherein the control traveler performs a relative motion with respect to the control track part during at least a part of the cocking phase, in which the control traveler travels along a control track of the control track part, wherein at least a part of the motion of the lancet dive is controlled.

2. The system according to claim 1, wherein the control track part is an input-side component of the track control mechanism coupled with the actuation element of the cocking mechanism.

3. The system according to claim 1, wherein the control track part or the control traveler is movably guided in the housing parallel to its longitudinal axis (A).

4. The system according to claim 1, wherein the actuation element includes a cocking button projecting from the rear end of the housing opposite front the exit opening.

5. The system according to claim 1, wherein the control track of the control track part includes a one-way section which is designed and arranged in such a manner that the control traveler, once it is driven into the one-way section, can be driven out of the one-way section only in one direction whereby a relative motion of the control traveler with respect to the control track part beyond the one-way section is possible only in one travel direction of the control track.

6. The system according to claim 1, wherein the control track of the control track part includes a reversing section, which is designed and arranged in such a manner that the control traveler, once it is driven into the reversing section, can he driven out of the reversing section only after the control traveler performs a relative motion with respect to the control track part in the reverse direction of its previous motion.

7. The system according to claim 1, wherein the motion of the lancet drive is controlled by the relative motion of the control traveler with respect to the control track part during at least a part of the cocking phase until the triggering of the drive phase.

8. The system according to claim 1, wherein the lancet drive includes a drive rotor which is driven by the drive spring and is rotatable about an axis wherein during the drive phase of the motion of the lancet drive the rotational motion of the drive rotor is converted by the output-side coupling mechanism into a puncturing motion.

9. The system according to claim 8, wherein one of the components of the track control mechanism is coupled to the drive rotor in such a manner that it rotates synchronous therewith.

10. The system according to claim 9, wherein the component of the track control mechanism which is coupled to the drive rotor is the control traveler.

11. The system according to claim 8, wherein the housing has an elongated shape the control track part or the control traveler is movably guided in the housing parallel to its longitudinal axis, the actuation element of the cocking mechanism is coupled to a force transmission part, which is guided within the housing such that it can be displaced in the longitudinal direction of the housing, and the rotation axis of the drive rotor extends transverse to the longitudinal axis of the housing.

12. The system according to claim 11, wherein the input-side coupling mechanism includes a toothed rack provided on the force transmission part, and a pinion gear which engages the toothed rack.

13. The system according to claims 8, wherein the output-side coupling mechanism includes a recess, which forms a guide curve, which recess is engaged by a guide pin, in such a manner that, during the rotational motion of the drive rotor in the drive phase, the guide pin travels along the guide curve formed by the recess, whereby at least a part of the motion of the lancet in the drive phase is controlled and the maximal displacement of the lancet in the puncturing direction is determined by a lower reversing point of the guide curve.

14. The system according to claim 8, wherein the end of the drive spring remote from the drive rotor abuts against a rotatable tensioning element, wherein the tensioning element can be rotated in the same rotation direction, in which the drive rotor rotates during the drive phase for tensioning of the drive spring, while the rotation of the drive rotor is inhibited, and the tensioning element is locked against a reverse motion during the drive phase such that the drive rotor performs, after release of the inhibition, a rotational motion which is transformed by the output-side coupling mechanism into the puncturing motion of the lancet.

15. The system according to claim 14, wherein the rotatable tensioning element and the drive rotor are components of a drive module which components are rotatable about a common axis (C).

16. The system according to claim 1, wherein the control track of the additional track control mechanism comprises a slide surface and the control traveler of the additional track control mechanism is pressed by spring action against said slide surface.

17. The system according to claim 1, wherein one of the control track part and the control traveler is coupled to the actuation element of the cocking mechanism such that it is moved synchronously with the actuation element, the input-side coupling mechanism comprises a three transmission part for effecting the transmission of force from the actuation element to the drive spring, and the at least one of the control track part and the control traveler and the force transmission part are connected to each other and are attached to the actuation element such that both parts are moved equally in a translational motion by actuation of the actuation element.

18. The system according to claim 1, wherein the drive phase is triggered by actuating said actuating element.

19. A blood withdrawal system for withdrawing blood for diagnostic purposes the system comprising:
a housing, wherein a lancet can be moved within the housing along a predetermined puncturing path to perform a puncturing motion;
a lancet drive with a drive spring and a cocking mechanism;
wherein the cocking mechanism includes an actuation element, which is coupled by an input-side coupling mechanism to the drive spring such that the drive spring is tensioned when the actuation element is moved during a cocking phase of the motion of the lancer drive;
wherein the drive spring is coupled by an output-side coupling mechanism to the lancet such that the lancet is, during a drive phase of the motion of the lancet drive driven by a relaxing motion of the drive spring, moved at high speed along the predetermined puncturing path to generate a wound; and
a lancet ejection mechanism, wherein the lancet ejection mechanism, includes a release element which is borne in the housing such that it can be switched between a passive position and an active position, wherein when the release element is in its active position such that actuating an actuation button of the lancet ejection mechanism removes a used lancet from the housing;
wherein the front end of the housing is formed by a cap, which can be removed in order to remove used lancets, such that when the cap is attached, the cap interacts with the release element such that it is in its passive position, and
wherein the release element is switched to its active position upon removal of the cap.

20. The system according to claim 19, wherein the release element is a part of a force transmission chain between the actuation button and a lancet, which three transmission chain is required for the ejection of the lancet.

21. The system according to claim 20, wherein the release element can be displaced in the same direction as the actuation button.

22. The system according to claim 20, wherein the three transmission chain is interrupted when the release element is in its passive position.

23. The system according to claim 19, wherein the actuation element of the cocking mechanism of the lancet drive is also the actuation button of the lancet ejection mechanism.

* * * * *